United States Patent [19]

Yoshida et al.

[11] Patent Number: 4,560,666
[45] Date of Patent: Dec. 24, 1985

[54] HIGH STRENGTH GLASS-CERAMIC CONTAINING APATITE AND ALKALINE EARTH METAL SILICATE CRYSTALS AND PROCESS FOR PRODUCING THE SAME

[75] Inventors: Masahiro Yoshida, Tokyo; Kenji Nakagawa, Saitama, both of Japan

[73] Assignee: Hoya Corporation, Tokyo, Japan

[21] Appl. No.: 678,977

[22] Filed: Dec. 6, 1984

[30] Foreign Application Priority Data

Dec. 20, 1983 [JP] Japan ................................ 58-238820
Dec. 22, 1983 [JP] Japan ................................ 58-240968

[51] Int. Cl.$^4$ ............................................. C03C 3/22
[52] U.S. Cl. .......................................... 501/5; 623/18; 65/33; 433/201.1; 501/10; 501/57; 501/58; 501/59; 501/63; 501/73; 501/77
[58] Field of Search .................. 501/5, 10, 73, 63, 57, 501/58, 59, 77; 3/1.91; 433/201, 202; 65/33

[56] References Cited

U.S. PATENT DOCUMENTS 3,881,945  5/1975  Trojer et al. ............................. 501/5
3,981,736  9/1976  Broemer et al. ...................... 501/10
4,365,356 12/1982  Broemer et al. ...................... 501/77
4,366,253 12/1982  Yagi et al. ............................. 501/63
4,437,192  3/1984  Fujiu et al. ............................ 501/63
4,483,678 11/1984  Nishio et al. .......................... 3/1.91

FOREIGN PATENT DOCUMENTS 57-191252 11/1982 Japan .

Primary Examiner—Helen M. McCarthy
Attorney, Agent, or Firm—Cushman, Darby & Cushman

[57] ABSTRACT

A high strength glass-ceramic containing apatite and alkaline earth metal silicate (diopside/forsterite/akermanite) crystals having an excellent affinity for a living body and a process for producing the same are disclosed. The glass-ceramic is useful as an implant material such as an artificial dental root and an artificial bone.

4 Claims, 4 Drawing Figures

HIGH STRENGTH GLASS-CERAMIC CONTAINING APATITE AND ALKALINE EARTH METAL SILICATE CRYSTALS AND PROCESS FOR PRODUCING THE SAME

FIELD OF THE INVENTION

The present invention relates to a high strength glass-ceramic containing apatite crystals which is useful as an implant material such as an artificial dental root and an artificial bone, and a process for producing the glass-ceramic.

BACKGROUND OF THE INVENTION

In recent years, an artificial material such as an artificial dental root or an artificial bone has been used as a substitute for a dental root or bone. Artificial materials which have heretofore been used for this purpose are anti-corrosive alloys such as a stainless steel and a cobalt/chromium alloy, and polymer such as polymethyl methacrylate and high density polyethylene. These materials, however, have a problem in that when those are used for a long period of time, metallic ions or monomers tend to elute in a living body and, therefore, those are sometimes harmful to a human body. On the other hand, a ceramic material generally exhibits an excellent biocompatibility to a living body and is stable in a living body. It has now received increasing attention as an artificial material.

One of such ceramic materials is single crystalline or polycrystalline alumina. This material is characterized by having a very high strength. The alumina ceramic, however, does not form any chemical bonding with a bone. To fix the alumina ceramic in a living body, therefore, a procedure should be employed in which the alumina ceramic itself is screwed or bored and physically fixed inside a bone. In this case, if the shape of the material is unsuitable, a stress sometimes concentrates in one part of the bone or material, resulting in the absorption of the bone and the formation of collagen fibers in the interface between the bone and the material. This makes loose the fixed part of the material or causes the material to come apart. In order to overcome the above problem, investigations have recently been made to develop ceramics which can form a chemical bonding with a bone and be firmly fixed inside the bone.

Typical examples of such ceramics are a sintered body of hydroxy-apatitie, a $Na_2O$—$CaO$—$P_2O_5$—$SiO_2$-based bioglass, and a glass-ceramic containing apatite crystals obtained by the precipitation of the apatite crystals from a $Na_2O$—$K_2O$—$MgO$—$CaO$—$P_2O_5$—$SiO_2$-based glass. Hydroxy apatite crystals, however, are converted into tricalcium phosphate when sintered at high temperatures. Consequently, it is difficult to produce a sintered hydroxy-apatite having a dense structure and a high strength. The bioglass and apatite-containing glass-ceramic have a disadvantage in that those can be utilized only in parts where only a small stress is applied, since its mechanical strength is low. In recent years, therefore, glass-ceramic has been developed which can form a chemical bonding with a bone and further has a relatively high strength.

Such a conventional glass-ceramic is produced by the following method: grinding $MgO$—$CaO$—$P_2O_5$—$SiO_2$-based glass with a MgO content of 7 wt% or less to 200 mesh or less powders, compression molding the glass powders and then heat treating the molding in the sintering temperature range of the glass powders and subsequently in the temperature range where apatite and wollastonite crystals are formed. The thus-obtained glass-ceramic has a bending strength of from 1,200 to 1,400 kg/cm². Of conventional materials forming a chemical bonding with a bone, the glass-ceramic has the highest strength. In this glass-ceramic, however, since the sintering temperature range of the glass powders is close to the crystal-precipitation temperature range, crystallization proceeds before air bubbles disappear by sintering. For this reason, it is difficult to produce the dense glass-ceramic having a high strength in every time. Thus, the above glass-ceramic has a disadvantage in that the strength varies depending on the production lot. Furthermore, when the glass-ceramic is used as an artificial dental root, it is desired to have a higher mechanical strength.

A glass-ceramic containing apatite crystals and alkaline earth metal silicate crystals such as diopside crystal, forsterite crystal and akermanite crystal is also known. This glass-ceramic is obtained by grinding a $MgO$—$CaO$—$SiO_2$—$P_2O_5$-based glass with the MgO content of 8 wt% or more to 200 mesh or less powders, molding the glass powders, heat treating the molding in the sintering temperature range of the glass powders (750° to 880° C.) and then heat treating the molding in the temperature range where apatite crystals ($Ca_{10}(PO_4)_6O$) and alkaline earth metal silicate crystals such as diopside ($MgOCaO2SiO_2$), forsterite ($2MgOSiO_2$) and akermanite ($2CaOMgO2SiO_2$) (830° to 1150° C.) are formed.

In this glass-ceramic, the apatite crystals act to improve the affinity with a living body and the alkaline earth metal silicate crystals act to increase the mechanical strength of the glass-ceramic. Therefore in order to obtain a glass-ceramic having a good affinity with a living body and a high mechanical strength, it is required for the glass-ceramic to contain the apatite crystals and alkaline earth metal silicate crystals as much as possible. However, in the conventional glass-ceramic of this type, if the heat treatment is conducted at high temperatures in order to increase the amount of alkaline earth metal silicate crystals formed, the apatite crystals which have been previously precipitated tend to decrease. Thus, those conventional glass-ceramic have the disadvantage in that if the amount of alkaline earth metal silicate crystals precipitated is increased thereby improving the mechanical strength, the apatite crystals decrease, resulting in lowering the affinity with a living body.

SUMMARY OF THE INVENTION

The present invention is intended to overcome the problems in the conventional glass-ceramic.

One object of the present invention is to provide a glass-ceramic which contains apatite crystals exhibiting an excellent affinity with a living body and has a high strength.

Another object of the present invention is to provide a process for producing the glass-ceramic.

The glass-ceramic of the present invention contains large amounts of apatite ($Ca_{10}(PO_4)_6O$) and at least one alkaline earth metal silicate crystals selected from the group consisting of diopside ($MgO.CaO.2SiO_2$), forsterite ($2MgO.SiO_2$) and akermanite ($2CaO.MgO.2SiO_2$) which are uniformly dispersed in the glass, and has a composition comprising, in % by weight, 8 to 34% MgO;

12 to 43% CaO;
25 to 40% SiO$_2$;
10 to 25% P$_2$O$_5$;
optionally 1 to 10% Al$_2$O$_3$ and/or ZrO$_2$;
with proviso of $$MgO+CaO+SiO+P_2O_5(+Al_2O_3 \text{ and/or } ZrO_2) \geqq 90\%,$$

0 to 10% Li$_2$O;
0 to 5% Na$_2$O;
0 to 10% K$_2$O;
0 to 10% SrO;
0 to 10% B$_2$O$_3$;
0 to 10% TiO$_2$;
0 to 10% Nb$_2$O$_5$;
0 to 10% Ta$_2$O$_5$; and
0 to 3% F$_2$,
with proviso of $$Li_2O+Na_2O+K_2O+SrO+B_2O_3+TiO_2+Nb_2O_5+Ta_2O_5+F_2 \leqq 10\%.$$

A process for producing the glass-ceramic according to the present invention comprises:
molding 200 mesh or less glass powders having the above composition;
heat treating the resulting molding within the sintering temperature range of the glass powders; and
further heat treating the molding within a temperature range where apatite crystals and alkaline earth metal silicate crystals such as diopside, forsterite and akermanite are formed.

BRIEF DESCRIPTION OF THE DRAWINGS

FIGS. 1 and 3 show the above relationship for apatite crystals;
and
FIGS. 2 and 4 show the above relationship for diopside and forsterite crystals.
Glass A: Glass not containing Al$_2$O$_3$
Glass B: Glass containing Al$_2$O$_3$
Glass C: Glass not containing ZrO$_2$
Glass D: Glass containing ZrO$_2$

DETAILED DESCRIPTION OF THE INVENTION

Figure 1:
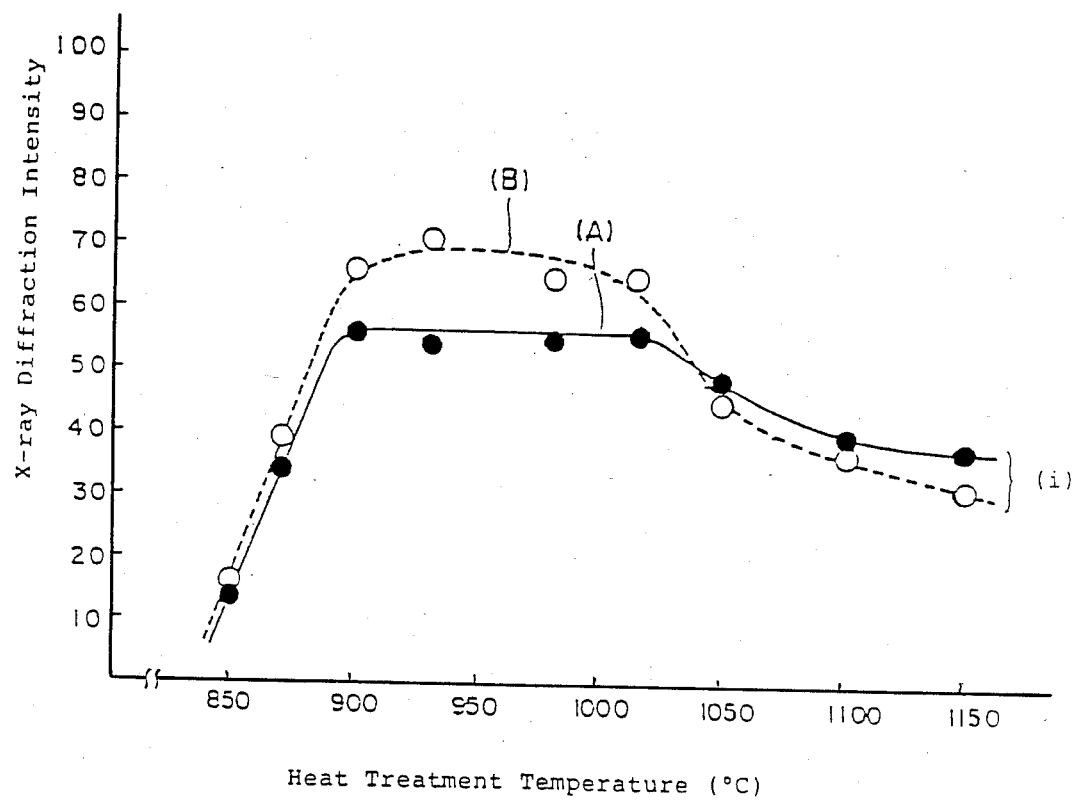
FIGS. 1 to 4 each shows a relationship between a heat-treatment temperature of an apatite crystal-containing high strength glass-ceramic of the present invention and an X-ray diffraction intensity of the crystal contained in the glass-ceramic.

The reason why the amount of each component of the glass-ceramic of the present invention is limited to the above-specified range will hereinafter be explained.

If the amount of MgO is less than 8%, the sintering temperature range of the resulting glass composition is close to a crystal-forming temperature range. Therefore, crystallization occurs before disappearance of air bubbles due to sintering and a glass-ceramic of dense structure is difficult to obtain. On the other hand, if the amount of MgO is more than 34%, the amount of apatite crystals formed is undesirably small. Thus, the MgO content is limited to a range of from 8 to 34%.

If the amount of CaO is less than 12%, the amount of apatite crystals formed is undesirably small. On the other hand, if the amount of CaO is more than 43%, devitrification tendency of glass is markable and the desired glass-ceramic is difficult to produce. Thus, the CaO content is limited to a range of from 12 to 43%.

If the amount of SiO$_2$ is less than 25%, devitrification of glass tends to occur and the desired glass-ceramic is difficult to produce. Moreover, since the amounts of calcium and magnesium (alkaline earth metals) silicate crystals formed are small, a glass-ceramic having a high strength is difficult to obtain. On the other hand, if the amount of SiO$_2$ is more than 40%, the resulting glass tends to occur phase separation and a uniform glass cannot be obtained. Thus, the SiO$_2$ content is limited to a range of from 25 to 40%.

If the amount of P$_2$O$_5$ is less than 10%, the apatite crystals are formed only in small amounts. On the other hand, if the amount of P$_2$O$_5$ is more than 25%, the phase separation occurs and a uniform glass cannot be obtained. Thus, the P$_2$O$_5$ content is limited to a range of from 10 to 25%.

A glass composition additionally containing Al$_2$O$_3$ provides the following effect, although it will be explained in detail later. That is, when the glass composition additionally containing Al$_2$O$_3$ is heated at a temperature of about 900° to 1,000° C., the apatite crystals are formed in a considerably greater amount than that in a glass composition not containing Al$_2$O$_3$. If the amount of Al$_2$O$_3$ added is less than 1%, the effect of accelerating the precipitation of apatite crystals is small. On the other hand, if the amount thereof is more than 10%, the amounts of alkaline earth metal silicate crystals formed are reduced. Thus, the Al$_2$O$_3$ content is limited to a range of from 1 to 10%.

A glass composition additionally containing ZrO$_2$ provides the following effect, although it will be explained in detail later. That is, if the amount of ZrO$_2$ added is less than 1%, the effect of accelerating the precipitation of apatite crystals is small. On the other hand, if the amount thereof is more than 10%, ZrO$_2$ does not dissolve in the glass. Thus, the amount of ZrO$_2$ added is limited to a range of from 1 to 10%, preferably from 3 to 6%.

The glass-ceramic of the present invention can contain, as well as the above-described components, one or more of compounds selected from the group consisting of Li$_2$O, Na$_2$O, K$_2$O, SrO, B$_2$O$_3$, TiO$_2$, Nb$_2$O$_5$, Ta$_2$O$_5$ and F$_2$, which are harmless to a human body, in a total amount of 10% or less. If the total amount of these additives is 10%, the amounts of apatite crystals and alkaline earth metal silicate crystals formed are reduced. Thus, the total amount of the additives is limited to 10% or less. Accordingly, the total amount of MgO, CaO, SiO$_2$ and P$_2$O$_5$, or the components plus Al$_2$O$_3$ and/or ZrO$_2$ is limited to at least 90%, preferably 95 to 98%.

The amount of Li$_2$O is 0 to 10%, preferably less than 4%.

The amount of Na$_2$O is 0 to 5%, preferably less than 4%. If the amount of Na$_2$O added is more than 5%, the amount of apatite crystals formed is markedly decreased.

The amount of K$_2$O is 0 to 10%, preferably less than 4%.

The amount of SrO is 0 to 10%, preferably less than 5%.

The amount of B$_2$O$_3$ is 0 to 10%, preferably less than 5%.

The amount of TiO$_2$ is 0 to 10%, preferably less than 5%.

The amount of Nb$_2$O$_5$ is 0 to 10%, preferably less than 5%.

The amount of $Ta_2O_5$ is 0 to 10%, preferably less than 5%.

The amount of $F_2$ is 0 to 3%, preferably less than 1.5%. If the amount of $F_2$ added is more than 3%, devitrification of glass occurs seriously.

The glass-ceramic having the above composition is produced in the following manner.

A glass having the above composition, either containing or not containing $Al_2O_3$ and/or $ZrO_2$, is ground to a particle size of 200 mesh or less and then molded into a desired form. If, on the other hand, the glass is molded into the desired form directly from a moleten state and then heat treated, although apatite crystals are precipitated in a uniformly dispersed condition, alkaline earth metal silicate crystals such as diopside, akermanite and forsterite, precipitate from the glass surface, forming cracks in the inside of the glass-ceramic. As a result, a glass-ceramic having a high strength cannot be obtained.

In order to obtain a glass-ceramic containing less air bubbles and crystals uniformly dispersed therein, it is a very important condition to employ a finely powdered glass. If the particle size of the glass powders is more than 200 mesh, large air bubbles tend to remain in a glass-ceramic obtained by sintering the glass powders and it is not possible to produce a glass-ceramic having a high mechanical strength. Therefore, the particle size of the powdered glass is limited to 200 mesh or less.

In order to produce the glass-ceramic of the present invention, it is also necessary that a molding of the above glass powders be subjected to a heat treatment within the sintering temperature range of the glass powders and then within a temperature range where apatite crystals and alkaline earth metal silicate crystals such as diopside are formed. A heat treatment of the glass powders within the sintering temperature range thereof is an important factor to obtain a glass-ceramic containing no air bubble and having a high mechanical strength.

The sintering temperature range of the glass powders can be determined by heating a molding of the glass powders at a constant temperature-raising speed and measuring a heat shrinkage of the molding due to the sintering thereof. The sintering temperature range is from a temperature at which the heat shrinkage starts to a temperature at which the heat shrinkage finishes.

A heat treatment within the apatite crystal-forming temperature range is important to precipitate a large amount of apatite crystals necessary for chemically bonding the resulting glass-ceramic to a bone. A heat treatment within the temperature range where alkaline earth metal silicate crystals such as diopside are formed is important to precipitate a large amount of alkaline earth metal silicate crystals, thereby increasing the mechanical strength of the resulting glass-ceramic. Each crystal-forming temperature range can be determined by a differential thermal analysis of the glass powders. A glass powders are heat treated at a temperature at which an exothermic peak appears in a differential thermal analytical curve and then is subjected to an X-ray diffraction analysis. By analyzing the data of the X-ray diffraction analysis, precipitated crystals corresponding to the exothermic peak are identified. The crystal-forming temperature range for each crystal is from a temperature at which heat-evolution starts to a temperature at which heat-evolution finishes.

The effect resulting from the addition of $Al_2O_3$ will hereinafter be explained by reference to FIGS. 1 and 2.

Figure 2:
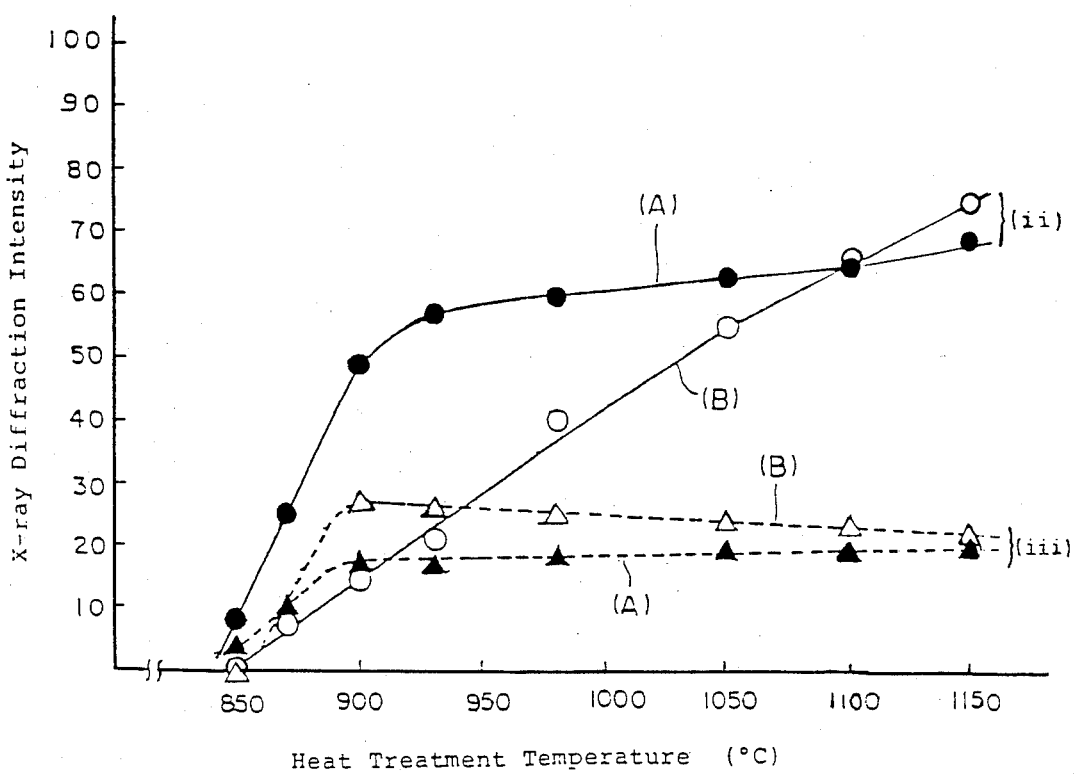

FIGS. 1 and 2 each shows a relationship between an intensity of an X-ray diffraction peak and a retention temperature for heat-treatment for Glass A not containing $Al_2O_3$ and Glass B containing $Al_2O_3$.

The curves indicated by the symbol (i) in FIG. 1 each represents a relationship between an intensity of a main X-ray diffraction peak (d=2.81 Å) of apatite crystals and a retention temperature for heat-treatment. Likewise, in FIG. 2, the symbols (ii) and (iii) represent, respectively, a relationship between an intensity of a main X-ray diffraction peak (d=2.99 Å) of diopside crystals and a retention temperature for heat-treatment, and a relationship between an intensity of a main X-ray diffraction peak (d=3.88 Å) of forsterite crystals and a retention temperature for heat-treatment.

Glass A has a composition comprising, in % by weight, 20.8% MgO, 29.2% CaO, 33.4% $SiO_2$, 16.1% $P_2O_5$ and 0.5% $F_2$. On the other hand, Glass B has the above composition to which 4% $Al_2O_3$ is additionally added. Each glass is ground to 200 mesh or less particles, heated in an electric furnace from room temperature at a temperature-rising rate of 10° C./min., maintaining at a constant temperature between 850° and 1,150° C. for 30 minutes, and then cooled to room temperature. Crystals precipitated from Glasses A and B after the heat-treatment are identified by the powder X-ray diffraction analytical method. In each sample, main crystals precipitated are apatite, diopside and forsterite.

The following can be seen from FIGS. 1 and 2. At retention temperatures below 1,015° C., the intensity of the main X-ray diffraction peak of apatite crystals of Glass B containing $Al_2O_3$ is about 23% greater than that of Glass A not containing $Al_2O_3$, viz., the amount of apatite formed in Glass B is greater than that in Glass A. On the other hand, at retention temperatures below 1,015° C., the amount of diopside crystals formed in Glass B is somewhat smaller than that in Glass A. However, the amount of forsterite crystals formed tends to increase to a certain extent. Thus, the total amount of diopside and forsterite formed in Glass B is nearly equal to that in Glass A. This demonstrates that addition of $Al_2O_3$ results in a considerable increase in the amount of apatite crystals formed. Thus, it can be understood that a crystallized glass as produced by heating a glass containing $Al_2O_3$ like Glass B at temperature of 1,015° C. or less contains a large amount of apatite crystals and, therefore, exhibits an excellent affinity for a living body.

Although the effect of adding $Al_2O_3$ has been explained above by reference to a glass having a certain definite composition, the effect of increasing the amount of apatite crystals precipitated by adding $Al_2O_3$ is not limited to the above composition. Further, the type of alkaline earth metal silicate crystals precipitated by the heat-treatment varies depending on the glass composition. That is, forsterite (2MgO.SiO$_2$) precipitates from a glass having a composition that the MgO content is high; diopside (CaO.MgO.2SiO$_2$), from a glass having a composition that the CaO content is high; and akermanite (2CaO.MgO.2SiO$_2$), from a glass having a composition that the SiO$_2$ content is small, or the P$_2$O$_5$ content is small. Two or more of the above crystals precipitate when the composition falls within intermediate regions. In the case that additives such as Na$_2$O, K$_2$O and Li$_2$O are added, crystals other than the above-described crystals sometimes precipitate.

The effect resulting from the addition of $ZrO_2$ will hereinafter be explained by reference to FIGS. 3 and 4.

Figure 3:
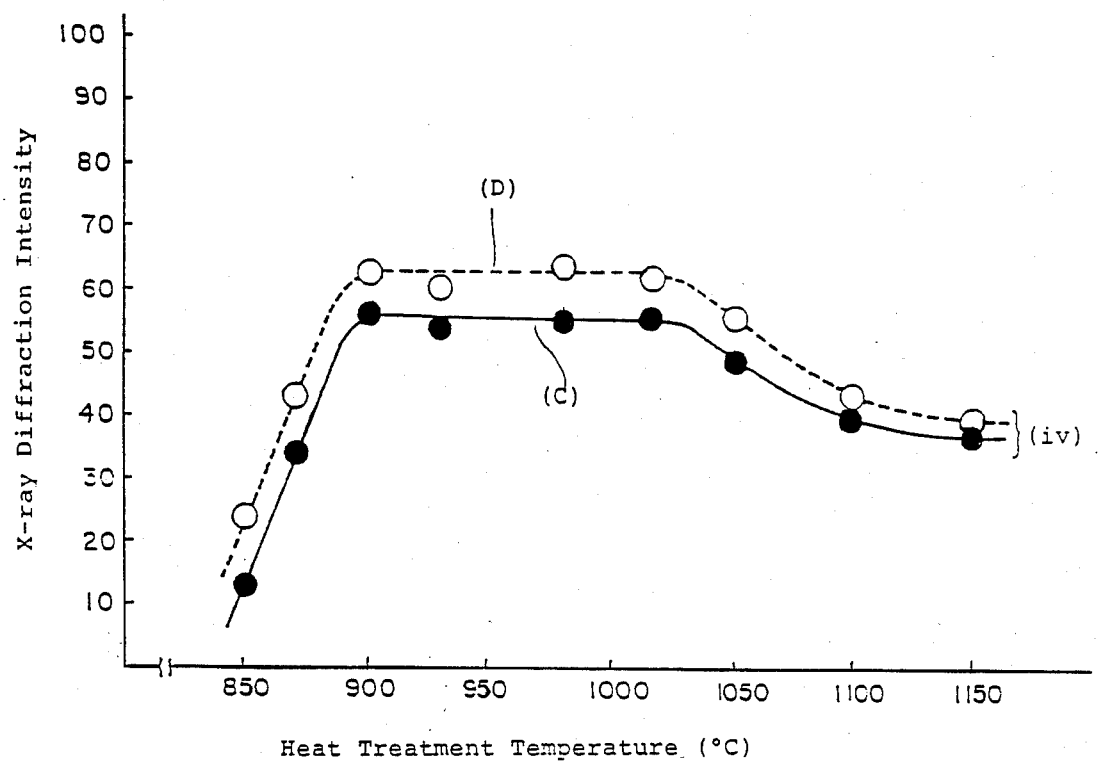
Figure 4:
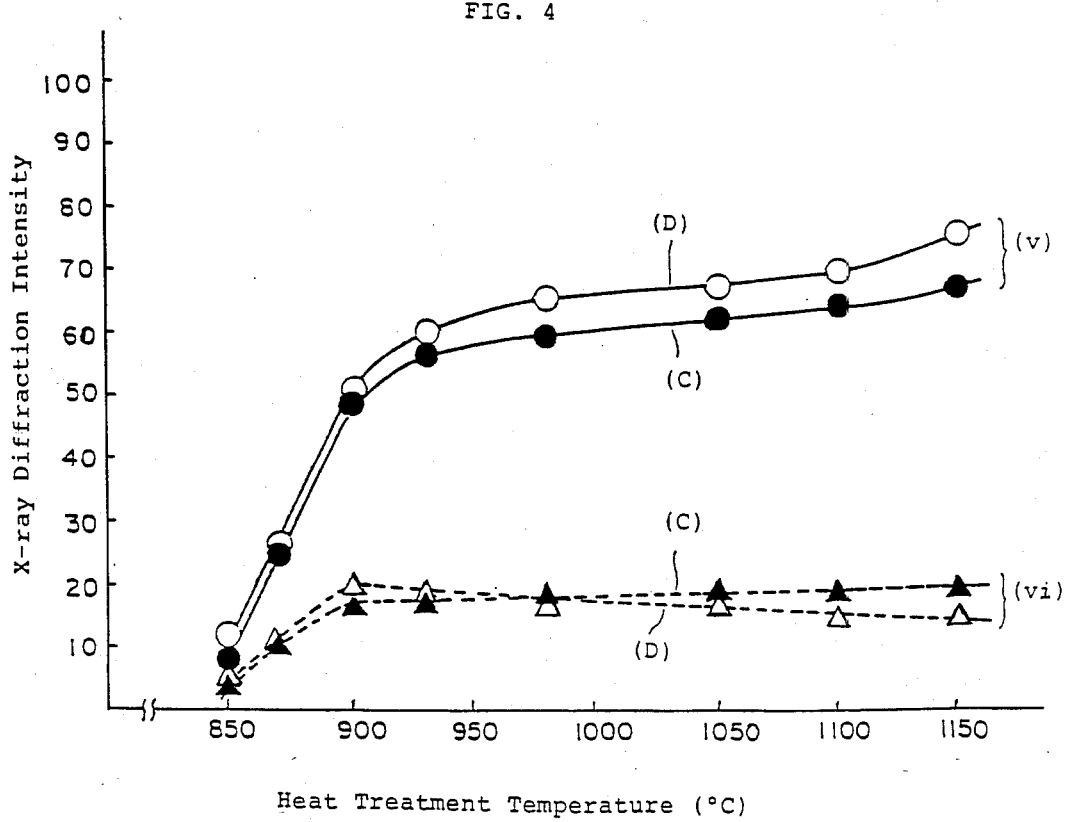

FIGS. 3 and 4 each shows a relationship between an intensity of an X-ray diffraction peak and a retention temperature for heat-treatment for Glass C not containing $ZrO_2$ and Glass D containing $ZrO_2$.

The curves indicated by the symbol (iv) in FIG. 3 each represents a relationship between an intensity of a main X-ray diffraction peak (d=2.81 Å) of apatite crystals and a retention temperature for heat-treatment. Likewise, in FIG. 4, the symbols (v) and (vi) represent, respectively, a relationship between an intensity of a main X-ray diffraction peak (d=2.99 Å) of diopside crystals and a retention temperature for heat-treatment, and a relationship between an intensity of a main X-ray diffraction peak (d=3.88 Å) of forsterite crystals and a retention temperature for heat-treatment.

Class C has a composition comprising, in % by weight, 20.8% MgO, 29.2% CaO, 33.4% $SiO_2$, 16.1% $P_2O_5$ and 0.5% $F_2$. On the other hand, Glass D has the above composition to which 4% $ZrO_2$ is additionally added. Each glass is ground to 200 mesh or less particles, heated in an electric furnace from room temperature at a temperature-rising rate of 10° C./min., maintaining at a constant temperature between 850° and 1,150° C. for 30 minutes, and then cooled to room temperature. Crystals precipitated from Glasses A and B after the heat-treatment are identified by the powder X-ray diffraction analytical method. In each sample, main crystals precipitated are apatite, diopside and forsterite.

As is apparent from curves (iii) in FIG. 3, the apatite crystals start to precipitate at 850° C. and the precipitation amount reaches a constant value at 900° C. However, the amount of apatite crystals gradually decreases at 1,015° C. or more. On the contrary, as is apparent from curves (iv) in FIG. 4, the amount of diopsite crystals precipitated rapidly increases up to 930° C., but the increase thereof is slight at more than 930° C. The amount of forsterite crystals precipitated does not almost change. In comparison between Glass C not containing $ZrO_2$ and Glass D containing $ZrO_2$, the diffraction intensity of the apatite crystals precipitated from Glass D containing 4% $ZrO_2$ is about 13% greater than that of Glass C not containing $ZrO_2$. Similarly, in the diffraction intensity of diopsite crystals, Glass D is about 8% greater than Glass C. In order to increase the mechanical strength of the glass-ceramic, it is necessary to precipitate diopside crystals and forsterite crystals as much as possible by heat treating at higher temperatures. However, the amount of the apatite crystal decreases, resulting in deterioration of the affinity for a living body. Addition of $ZrO_2$ as in Glass D is very effective to increase the amount of diopside crystals without decreasing the amount of apatite crystals. In producing the glass-ceramic, the glass is kept at the maximum temperature (1,020° C.) where the apatite crystals are present stably, for 2 hours. Under the production conditions, the addition effect of $ZrO_2$ is remarkable as the retention time becomes longer. When examining crystals precipitated in the glass-ceramic obtained by molding glass powders of each of Glasses C and D, heating each molding at the temperature-rising rate of 3° C./min. and maintaining the molding at 1,020° C. for 2 hours, the diffraction intensity of apatite crystals of the crystallized glass containing 4% $ZrO_2$ is 20% greater than that of the glass-ceramic not containing $ZrO_2$, and the diffraction intensity of diopside crystals of the glass-ceramic containing 4% $ZrO_2$ is 5% greater than that of the crystallized glass not containing $ZrO_2$.

Thus, $ZrO_2$ acts effectively to obtain a glass-ceramic having a good affinity for a living body and a high mechanical strength.

The mother glass of the glass-ceramic of the present invention can be melted at 1,400° to 1,500° C. in a refractory crucible or platinum crucible as in the general glass, using oxides, phosphates, carbonates, fluorides, and the like as starting materials. The molten glass is quenched by flowing over a mold, or passing between cooled rollers, or pouring in water. The thus-obtained glass is then pulverized to 200 mesh or less particles by means of the usual pulverizer such as a pot mill or a jet mill. If necessary, the glass powders are screened to obtain particles having various sizes which are then compounded approximately. The glass powders are molded by procedures generally employed in molding of ceramics, such as press-molding using a metallic mold, slurry cast-molding, extrusion molding, and hydrostatic press-molding. In order to improve rheological properties such as flowability of powder in the molding process, it is effective to add conventional molding aids such as paraffin and stearic acid salts to the glass powders. Another effective method of improving the flowability of glass powders is to granulate the glass powders, i.e., use in a granular form.

Sintering and crystallization of a molding of the glass powders can be achieved by a method in which the glass powders are maintained at temperatures falling within the sintering temperature range of the glass powders, the apatite crystal-forming temperature range, and the alkaline earth metal silicate crystal-forming temperature range as described above, or a method in which the glass powders are gradually heated from the sintering temperature range of the glass powders to the alkaline earth metal silicate crystal-forming temperature range. Moreover, the sintering and crystallization of the glass powders by techniques such as a high temperature press molding method and a hot isostatic press method is effective to obtain a glass-ceramic having a dense structure.

The present invention is described in greater detail by reference to the following examples. Compositions are expressed in % by weight.

EXAMPLES

Glass compositions as shown in the Tables 1 and 2 below were prepared using oxides, carbonates, phosphates, fluorides and the like. Each glass composition was placed in a platinum crucible and melted at 1,400° to 1,500° C. for 1 hour. The thus-obtained glass was quenched by pouring it into water in the molten state and dried. It was then placed in a pot mill and pulverized to a size of 350 mesh or less. A mixture of the glass powders and 5 wt% of paraffin as a binder was placed in a metallic mold and press-molded into a desired form under a pressure of 600 kg/cm². The molding was placed in an electric furnace, and heated from room temperature to a prescribed temperature between 950° and 1,050° C. at a constant temperature-rising rate of 3° C./min. and maintained at that temperature for 2 hours to achieve sintering and crystallization. Then, the molding was gradually cooled to room temperature in the furnace.

The glass-ceramic was ruptured, and the rupture cross-section was examined by SEM. It was found that the glass-ceramic had a dense structure that almost no air bubble could be found. The glass sample was pulverized, and precipitated crystals were identified by X-ray diffraction analysis. In all cases, it was observed that, together with a large amount of apatite crystals, large amounts of alkaline earth metal silicate crystals such as diopside, forsterite and akermanite precipitated. The type of crystals precipitated is also shown in Tables 1 and 2 below.

Some samples were measured for a bending strength by using a 5×5×25 mm prism the surface of which was polished with No. 1000 aluminum abrasive particles. The results are also shown in Tables 1 and 2 below. As can be seen from Table 1, the glass-ceramic of the present invention has a bending strength as high as from 1,500 to 1,800 kg/cm².

TABLE 1

| | Example No. | | | | | |
|---|---|---|---|---|---|---|
| | 1 | 2 | 3 | 4 | 5 | 6 |
| MgO | 8.0 | 12.1 | 20.1 | 20.8 | 19.9 | 20.1 |
| CaO | 42.9 | 36.2 | 28.1 | 29.2 | 28.0 | 28.1 |
| $SiO_2$ | 32.9 | 32.1 | 32.2 | 33.3 | 32.0 | 32.2 |
| $P_2O_5$ | 15.7 | 15.6 | 15.6 | 16.2 | 15.6 | 15.6 |
| Additives | $F_2$ 0.5 | SrO 4.0 | $B_2O_3$ 4.0 | $F_2$ 0.5 | $Al_2O_3$ 4.0 $F_2$ 0.5 | $TiO_2$ 4.0 |
| Temperature-Rising Rate (°C./min.) | 3 | 3 | 3 | 3 | 3 | 3 |
| Retention Temperature (°C.) | 1030 | 1030 | 1000 | 1020 | 990 | 1000 |
| Retention Time (hr) | 2 | 2 | 2 | 2 | 2 | 2 |
| Type of Crystals Precipitated | Apatite Diopside | Apatite Diopside β-Tricalcium Phosphate | Apatite Diopside Forsterite β-Tricalcium Phosphate | Apatite Diopside Forsterite | Apatite Diopside Forsterite | Apatite Diopside Forsterite β-Tricalcium Phosphate |
| Bending Strength (kg/cm²) | 1800 | — | — | 1800 | 1600 | 1500 |

| | Example No. | | | | | |
|---|---|---|---|---|---|---|
| | 7 | 8 | 9 | 10 | 11 | 12 |
| MgO | 29.2 | 12.1 | 12.1 | 21.9 | 18.6 | 28.7 |
| CaO | 16.6 | 40.2 | 40.2 | 30.6 | 26.1 | 24.6 |
| $SiO_2$ | 37.5 | 28.1 | 28.1 | 35.0 | 29.8 | 28.7 |
| $P_2O_5$ | 16.2 | 15.6 | 15.6 | 12.0 | 23.0 | 16.0 |
| Additives | $F_2$ 0.5 | $Nb_2O_5$ 4.0 | $Ta_2O_5$ 4.0 | $F_2$ 0.5 | $F_2$ 0.5 $Li_2O$ 2.0 | $K_2O$ 2.0 |
| Temperature-Rising Rate (°C./min.) | 3 | 3 | 3 | 3 | 3 | 3 |
| Retention Temperature (°C.) | 950 | 1000 | 1000 | 1000 | 1000 | 1000 |
| Retention Time (hr) | 2 | 2 | 2 | 2 | 2 | 2 |
| Type of Crystals Precipitated | Apatite Diopside Forsterite | Apatite Akermanite Diopside β-Tricalcium Phosphate Forsterite | Apatite Akermanite Diopside β-Tricalcium Phosphate Forsterite | Apatite Akermanite Diopside β-Tricalcium Phosphate Forsterite | Apatite Akermanite Diopside β-Tricalcium Phosphate Forsterite | Apatite Forsterite Diopside β-Tricalcium Phosphate |
| Bending Strength (kg/cm²) | 1500 | 1500 | — | 1700 | — | — |

TABLE 2

| | Example No. | | | | | | | |
|---|---|---|---|---|---|---|---|---|
| | 13 | 14 | 15 | 16 | 17 | 18 | 19 | 20 |
| MgO | 20.1 | 19.9 | 12.0 | 28.0 | 12.0 | 27.8 | 12.4 | 12.0 |
| CaO | 28.1 | 28.0 | 36.0 | 15.9 | 40.0 | 23.9 | 36.9 | 35.8 |
| $SiO_2$ | 32.2 | 32.0 | 32.0 | 36.0 | 28.0 | 27.8 | 32.8 | 31.8 |
| $P_2O_5$ | 15.6 | 15.6 | 15.5 | 15.6 | 15.5 | 15.5 | 15.9 | 15.4 |
| $ZrO_2$ | 4.0 | 4.0 | 4.0 | 4.0 | 4.0 | 4.0 | 2.0 | 5.0 |
| Additives | — | $F_2$ 0.5 | $F_2$ 0.5 | $F_2$ 0.5 | $F_2$ 0.5 | $Na_2O$ 1.0 | — | — |
| Temperature-Rising Rate (°C./min.) | 3 | 3 | 3 | 3 | 3 | 3 | 3 | 3 |
| Retention Temperature (°C.) | 1000 | 1020 | 1000 | 1000 | 1000 | 1000 | 1000 | 1000 |
| Retention Time (hr) | 2 | 2 | 2 | 2 | 2 | 2 | 2 | 2 |
| Type of Crystals Precipitated | Apatite Diopside Forsterite β-Tricalcium Phosphate | Apatite Diopside Forsterite | Apatite Diopside | Apatite Forsterite Diopside | Apatite Diopside Akermanite Forsterite | Apatite Forsterite Diopside β-Tricalcium Phosphate | Apatite Diopside Forsterite β-Tricalcium Phosphate | Apatite Diopside Forsterite β-Tricalcium Phosphate |
| Bending Strength (kg/cm²) | 1800 | 2100 | 1500 | — | — | — | 1600 | 1800 |

| | Example No. | | | | | | |
|---|---|---|---|---|---|---|---|
| | 21 | 22 | 23 | 24 | 25 | 26 | 27 |
| MgO | 11.7 | 28.1 | 28.1 | 28.1 | 28.1 | 28.1 | 28.1 |
| CaO | 35.1 | 24.1 | 24.1 | 24.1 | 24.1 | 24.1 | 24.1 |
| $SiO_2$ | 31.1 | 28.1 | 28.1 | 28.1 | 28.1 | 28.1 | 28.1 |

TABLE 2-continued

| | | | | | | | |
|---|---|---|---|---|---|---|---|
| P$_2$O$_5$ | 15.1 | 15.7 | 15.7 | 15.7 | 15.7 | 15.7 | 15.7 |
| ZrO$_2$ | 7.0 | 2.0 | 2.0 | 2.0 | 2.0 | 2.0 | 2.0 |
| Additives | — | TiO$_2$ 2.0 | SrO 2.0 | Ta$_2$O$_5$ 2.0 | Nb$_2$O$_5$ 2.0 | K$_2$O 2.0 | B$_2$O$_3$ 2.0 |
| Temperature-Rising Rate (°C./min.) | 3 | 3 | 3 | 3 | 3 | 3 | 3 |
| Retention Temperature (°C.) | 1000 | 1000 | 1000 | 1000 | 1000 | 1000 | 1000 |
| Retention Time (hr) | 2 | 2 | 2 | 2 | 2 | 2 | 2 |
| Type of Crystals Precipitated | Apatite Dopside Forsterite β-Tricalcium Phosphate | Apatite Diopside Forsterite β-Tricalcium Phosphate | Apatite Diopside Forsterite β-Tricalcium Phosphate | Apatite Diopside Forsterite β-Tricalcium Phosphate | Apatite Diopside Forsterite β-Tricalcium Phosphate | Apatite Dopside Forsterite β-Tricalcium Phosphate | Apatite Diopside Forsterite β-Tricalcium Phosphate |
| Bending Strength (kg/cm$^2$) | 1500 | — | — | — | 1500 | — | — |

The glass-ceramic of the present invention contains a large amount of apatite crystals necessary for chemically bonding to a bone and has a very high bending strength of from 1,500 to 1,800 kg/cm$^2$. On the other hand, the conventional products such as a sintered body of a hydroxide apatite, a Na$_2$O—CaO—P$_2$O$_5$—SiO$_2$-based bioglass, a Na$_2$O—K$_2$O—MgO—CaO—P$_2$O$_5$—SiO$_2$-based glass-ceramic containing apatite crystals alone, and a glass-ceramic containing apatite and a wollastonite crystals have a bending strength ranging between 700 and 1,400 kg/cm$^2$. It can be therefore understood that the glass-ceramic of the present invention has a very high bending strength. Furthermore, in the glass-ceramic of the present invention, the bending strength does not almost vary depending on the production lot. Thus, the glass-ceramic of the present invention is very useful as a material for an artificial bone and an artificial dental root.

While the invention has been described in detail and with reference to specific embodiments thereof, it will be apparent to one skilled in the art that various changes and modifications can be made therein without departing from the spirit and scope thereof.

What is claimed is:

1. A high strength glass-ceramic having a bending strength from at least 1500 kg/cm$^2$ and containing apatite crystals and at least one alkaline earth metal silicate crystal selected from the group consisting of diopside, forsterite and akermanite and having a composition consisting essentially of, in % by weight, 8 to 34% MgO;
12 to 43% CaO;
25 to 40% SiO$_2$;
10 to 25% P$_2$O$_5$;
  with proviso of 90% or more MgO+CaO+SiO+P$_2$O$_5$,
0 to 10% Li$_2$O;
0 to 5% Na$_2$O;
0 to 10% K$_2$O;
0 to 10% SrO;
0 to 10% B$_2$O$_3$;
0 to 10% TiO$_2$;
0 to 10% Nb$_2$O$_5$;
0 to 10% Ta$_2$O$_5$; and
0 to 3% F$_2$,
  with proviso of 10% or less Li$_2$O+Na$_2$O+K$_2$O+SrO+B$_2$O$_3$+TiO$_2$+Nb$_2$O$_5$+Ta$_2$O$_5$+F$_2$.

2. A process for producing a high strength glass-ceramic containing apatite crystals and at least one alkaline earth metal silicate crystal, which process comprises molding glass powders having a particle size of 200 mesh or less and having a composition consisting essentially of, in % by weight, 8 to 34% MgO;
12 to 43% CaO;
25 to 40% SiO$_2$;
10 to 25% P$_2$O$_5$;
  with proviso of 90% or more MgO+CaO+SiO+P$_2$O$_5$,
0 to 10% Li$_2$O;
0 to 5% Na$_2$O;
0 to 10% K$_2$O;
0 to 10% SrO;
0 to 10% B$_2$O$_3$;
0 to 10% TiO$_2$;
0 to 10% Nb$_2$O$_5$;
0 to 10% Ta$_2$O$_5$; and
0 to 3% F$_2$,
  with proviso of 10% or less Li$_2$O+Na$_2$O+K$_2$O+SrO+B$_2$O$_3$+TiO$_2$+Nb$_2$O$_5$+Ta$_2$O$_5$+F$_2$,
heat treating the resulting molding in a sintering temperature range of the glass powders, and
heat treating the molding in the temperature range where alkaline earth metal silicate crystals selected from the group consisting of diopside, forsterite and akermanite are formed.

3. A high strength glass-ceramic having a bending strength from at least 1500 kg/cm$^2$ and containing apatite crystals and at least one alkaline earth metal silicate crystal selected from the group consisting of diopside, forsterite and akermanite and having a composition consisting essentially of, in % by weight, 8 to 34% MgO;
12 to 43% CaO;
25 to 40% SiO$_2$;
10 to 25% P$_2$O$_5$;
1 to 10% Al$_2$O$_3$, ZrO$_2$ or both
  with proviso of 90% or more MgO+CaO+SiO+P$_2$O$_5$+(Al$_2$O$_3$+ZrO$_2$),
0 to 10% Li$_2$O;
0 to 5% Na$_2$O;
0 to 10% K$_2$O;
0 to 10% SrO;
0 to 10% B$_2$O$_3$;
0 to 10% TiO$_2$;
0 to 10% Nb$_2$O$_5$;
0 to 10% Ta$_2$O$_5$; and
0 to 3% F$_2$,
  with proviso of 10% or less Li$_2$O+Na$_2$O+K$_2$O+SrO+B$_2$O$_3$+TiO$_2$+Nb$_2$O$_5$+Ta$_2$O$_5$+F$_2$.

4. A process for producing a high strength glass-ceramic containing apatite crystals and at least one alkaline earth metal silicate crystal, which process comprises
(1) molding glass powders having a particle size of 200 mesh or less and having a composition consisting essentially of, in % by weight,
8 to 34% MgO;
12 to 43% CaO;
25 to 40% $SiO_2$;
10 to 25% $P_2O_5$;
1 to 10% $Al_2O_3$, $ZrO_2$ or both
with proviso of 90% or more $MgO+CaO+SiO+P_2O_5+(Al_2O_3+ZrO_2)$,
0 to 10% $Li_2O$;
0 to 5% $Na_2O$;
0 to 10% $K_2O$;
0 to 10% SrO;
0 to 10% $B_2O_3$;
0 to 10% $TiO_2$;
0 to 10% $Nb_2O_5$;
0 to 10% $Ta_2O_5$; and
0 to 3% $F_2$,
with proviso of 10% or less $Li_2O+Na_2O+K_2O+SrO+B_2O_3+TiO_2+Nb_2O_5+Ta_2O_5+F_2$,
(2) heat treating the resulting molding in a sintering temperature range of the glass powders, and
(3) heat treating the molding in the temperature range where alkaline earth metal silicate crystals selected from the group consisting of diopside, forsterite and akermanite are formed.

* * * * *